US00PP12654P2

(12) United States Plant Patent
Scheffers

(10) Patent No.: US PP12,654 P2
(45) Date of Patent: May 28, 2002

(54) DRACAENA PLANT NAMED 'LEMON SURPRISE'

(76) Inventor: Ruud A.M. Scheffers, De Plaats 9, 2675 CK Honselersdijk (NL)

( * ) Notice: Subject to any disclaimer, the term of this patent is extended or adjusted under 35 U.S.C. 154(b) by 0 days.

(21) Appl. No.: 09/326,614

(22) Filed: Jun. 7, 1999

(51) Int. Cl.[7] ..... A01H 5/00

(52) U.S. Cl. ..... Plt./383

(58) Field of Search ..... Plt./383

(56) References Cited

PUBLICATIONS

Extract from the Register of Community Plant Variety Rights, 'LEMON SURPRISE', File No. 1998/1671, Applied for: Nov. 26, 1998; Grant No.: E.U. 6715 (Oct. 2, 2000).

*Primary Examiner*—Bruce R. Campell
*Assistant Examiner*—Susan B. McCormick
(74) *Attorney, Agent, or Firm*—Foley & Lardner

(57) ABSTRACT

A distinct Dracaena plant named 'Lemon Surprise' characterized by its 10 inch long leaves which are elliptic and elongated; lightly-curled leaf-edge; compact plant growth; and distinctive leaves which have a grey-green center (RHS 189B) a width at the center of approximately 1.5 cm; a white (RHS 155C) margin on both sides of the grey-green center which is approximately 0.1 cm wide and a yellow-green (RHS 144B) which are outer margins approximately 1.5 cm wide at the center of the leaf.

1 Drawing Sheet

BACKGROUND OF THE INVENTION

The present invention comprises a new and distinct cultivar of Dracaena plant botanically known as *Dracaena Vand. Ex. L. fragrans* (group Compacta) and hereinafter referred to by the cultivar name 'Lemon Surprise'.

The new cultivar was selected by the inventor, Ruud A. M. Scheffers, in Honselersdijk, The Netherlands, in April of 1996. The new cultivar was obtained as a mutation of *Dracaena Vand. Ex. L. fragrans* (group Compacta) 'Surprise' (unpatented). This new variety was a natural mutation in the form of a sport. The new cultivar was first asexually propagated by the inventor in Honselersdijk, The Netherlands, in April of 1996. Subsequent asexual reproduction of the new cultivar by division has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and in combination distinguish 'Lemon Surprise' as a new and distinct cultivar:

1. 10 inch long leaves which are elliptic and elongated;
2. Lightly-curled leaf-edge;
3. Compact plant growth; and
4. Distinctive leaves which have a grey-green (RHS 189B and 189C) center and approximately 1.5 cm wide in center of leaf; the grey-green center has a white (RHS 155C) margin on both sides which is approximately 0.1 cm wide and a yellow-green margin (RHS 144B) which is approximately 1.5 cm wide at the center of the leaf.

'Lemon Surprise' has not been observed under all possible environmental conditions. The phenotype of the new cultivar may vary significantly with variations in environment such as temperature, light intensity, and daylength, without any change in genotype. The following observations, measurements and values describe plants grown in The Netherlands under greenhouse conditions which closely approximate those generally used in horticultural practice.

In comparison with the well-known Dracaena cultivar 'Lemon Lime' (unpatented). 'Lemon Surprise' has shorter leaves, by 6 inches, with a more curly leaf-edge. 'Lemon Surprise' grows more compact than 'Lemon Lime'. 'Lemon Surprise' grows less compact than 'Surprise'. 'Surprise' has a wider white margin and the edge-margin is smaller than 'Lemon Surprise'.

BRIEF DESCRIPTION OF THE DRAWING

The accompanying photograph illustrates a one year-old mother plant of Dracaena 'Lemon Surprise' in a plant bed, with colors being as true as possible with illustrations of this type.

DETAILED BOTANICAL DESCRIPTION

The age of the plants described is 4 months old, as grown in The Netherlands.

Color references are made to The Royal Horticultural Society Colour Chart (R.H.S.), except where general colors of ordinary significance are used. Colors are approximate as color depends on horticultural practices such as light level and fertilization rate, among others.

Classification:

*Botanical.*—*Dracaena Vand. Ex. L. fragrans* (group Compacta).

*Commercial.*—Dracaena 'Lemon Surprise'.

Parentage: Mutant from *Dracaena Vand. Ex. L. fragrans* (group Compacta) 'Surprise'.

Propagation: Primarily by vegetative division of the plant head or apical meristem.

Plant habit:

*Growth rate.*—Medium to fast; approximately 20 weeks to obtain a mature plant from a cutting.

*Vigor.*—It takes 4 months for the plant to grow into a fully mature plant with a plant height of 38 to 40 cm.

*Form.*—Compact.

*Plant height.*—Approximately 15 to 20 cm above the soil surface, when the plant is grown for 150 days in a 4¾-inch pot in The Netherlands. A fully mature plant has a plant height of 38–40 cm.

*Plant width.*—Approximately 30 cm.

Leaves:

*Form and size.*—Elliptic, elongated and lightly curled, approximately 10 inches in length and up to 2.0 inches in width. Texture: Thick and leather-like.Veins: Only slightly visible near the bottom of the leaf, color of the main vein is RHS 189B and 189C.

*Color.*—Grey-green (RHS 189B and 189C) center and approximately 1.5 cm wide in center of leaf; the grey-geeen center has a white (RHS 155C) margin on both sides which is approximately 0.1 cm wide and a yellow-green margin (RHS 144B) which is approximately 1.5 cm wide at the center of the leaf. Leaf tip is 144B.

*Margin.*—Entire.

*Thickness.*—Medium.

*Number.*—Approximately 24 leaves per plant when grown in a 4¾ inch pot for approximately 150 days in The Netherlands.

Stem:

*Thickness.*—Approximately 0.5 inch, formed by bases of leaves.

*Color.*—Grey-green (RHS 189 B) in center and white and yellow-green (RHS 144 B) near edge.

Roots: Root initiation time is 3 weeks under Dutch growing conditions; color is orange-brown (RHS 175 A to RHS 175 B).

Plant disease and insect tolerance: No special observations made.

I claim:

1. A new and distinct cultivar of Dracaena plant named 'Lemon Surprise', as described and illustrated herein.

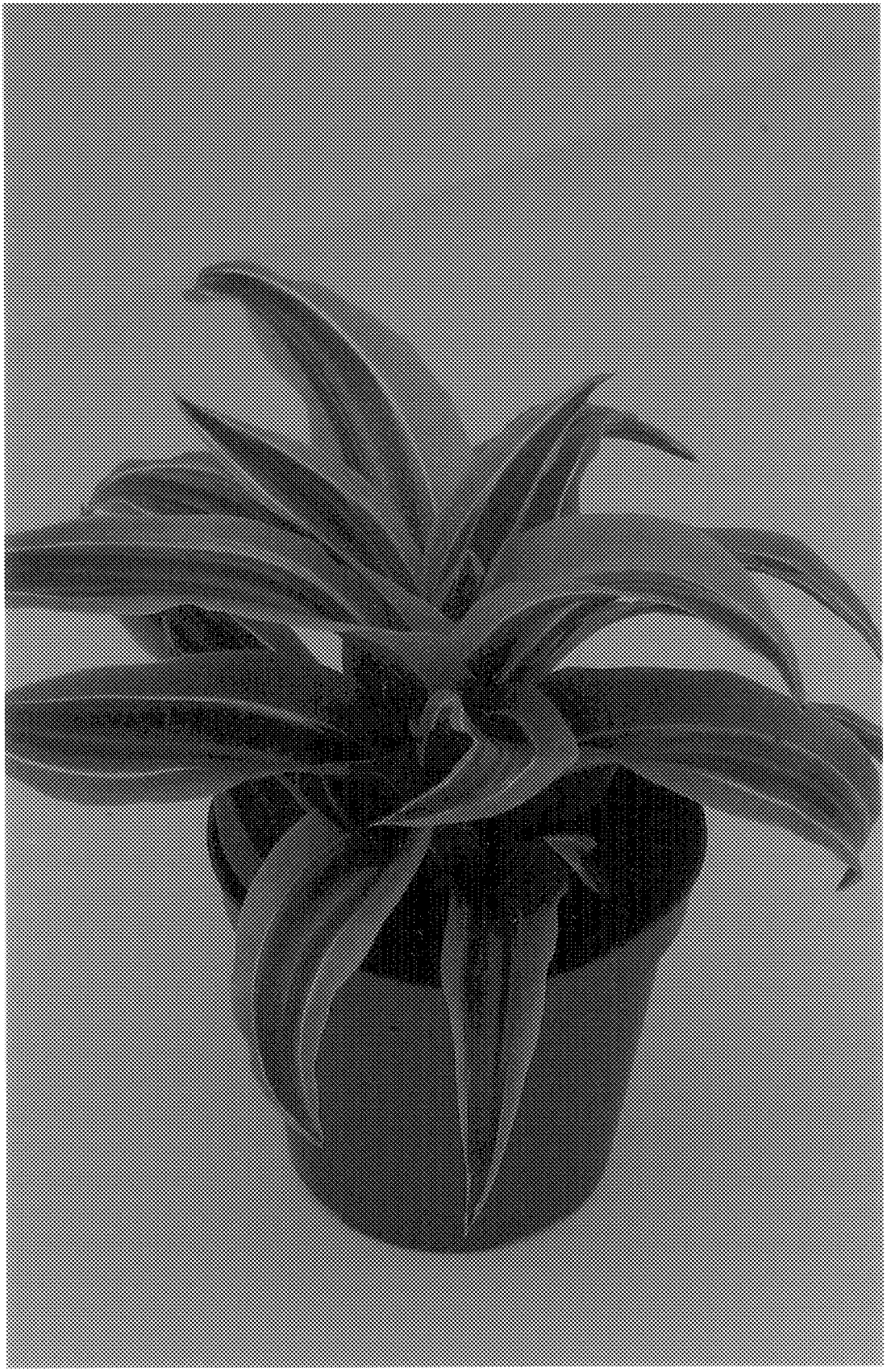

* * * * *